United States Patent
McKenna

(10) Patent No.: US 8,798,704 B2
(45) Date of Patent: Aug. 5, 2014

(54) PHOTOACOUSTIC SPECTROSCOPY METHOD AND SYSTEM TO DISCERN SEPSIS FROM SHOCK

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 550 days.

(21) Appl. No.: 12/880,308

(22) Filed: Sep. 13, 2010

(65) Prior Publication Data

US 2011/0071598 A1    Mar. 24, 2011

Related U.S. Application Data

(60) Provisional application No. 61/245,580, filed on Sep. 24, 2009.

(51) Int. Cl.
*A61B 5/026* (2006.01)

(52) U.S. Cl.
USPC .............................. 600/326; 607/62

(58) Field of Classification Search
USPC .............................. 607/62; 600/326
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,817,623 A | 4/1989 | Stoddart et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |

(Continued)

FOREIGN PATENT DOCUMENTS

| | | |
|---|---|---|
| AU | 732799 | 5/2001 |
| DE | 19640807 | 9/1997 |

(Continued)

OTHER PUBLICATIONS

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Aoyagi, T., et al.; "Analysis of Motion Artifacts in Pulse Oximetry," *Japanese Society ME*, vol. 42, p. 20 (1993) (Article in Japanese—contains English summary of article).

Aoyagi, Takuo; "Pulse oximetry: its invention, theory, and future," *Journal of Anesthesia*, vol. 17, pp. 259-266 (2003).

(Continued)

*Primary Examiner* — Christopher D Koharski
*Assistant Examiner* — Michael Carey
(74) *Attorney, Agent, or Firm* — Fletcher Yoder PC

(57) ABSTRACT

According to various embodiments, a medical system and method for determining a microcirculation parameter of a patient may include a photoacoustic sensor. Specifically, a signal from a photoacoustic sensor may be used to determine if a patient is likely to have sepsis or shock. Although sepsis and shock present similarly with regard to many patient parameters, they may be differentiated by characteristic microcirculation changes.

16 Claims, 3 Drawing Sheets

(56) References Cited

U.S. PATENT DOCUMENTS

| | | |
|---|---|---|
| 5,140,989 A | 8/1992 | Lewis et al. |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,349,961 A | 9/1994 | Stoddart et al. |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Keunstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,309,352 B1 | 10/2001 | Oraevsky et al. |
| 6,312,393 B1 | 11/2001 | Abreu |
| 6,353,750 B1 | 3/2002 | Kimura et al. |
| 6,397,091 B2 | 5/2002 | Diab et al. |
| 6,405,069 B1 | 6/2002 | Oraevsky et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,839,496 B1 | 1/2005 | Mills et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,020,506 B2 | 3/2006 | Fine et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,127,278 B2 | 10/2006 | Melker et al. |
| 7,162,306 B2 | 1/2007 | Caby et al. |
| 7,184,148 B2 | 2/2007 | Alphonse |
| 7,209,775 B2 | 4/2007 | Bae et al. |
| 7,236,811 B2 | 6/2007 | Schmitt |
| 7,254,432 B2 | 8/2007 | Fine |
| 7,263,395 B2 | 8/2007 | Chan et al. |
| 7,272,426 B2 | 9/2007 | Schmid |
| 7,327,463 B2 | 2/2008 | Alphonse |
| 7,356,365 B2 | 4/2008 | Schurman |
| 7,373,193 B2 | 5/2008 | Al-Ali et al. |
| 7,447,388 B2 | 11/2008 | Bates et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0095077 A1* | 7/2002 | Swedlow et al. ............ 600/323 |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |

(56) References Cited

U.S. PATENT DOCUMENTS

| | | |
|---|---|---|
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0054907 A1 | 3/2005 | Page et al. |
| 2005/0065556 A1 | 3/2005 | Reghabi et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0175540 A1 | 8/2005 | Oraevsky et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0063992 A1 | 3/2006 | Yu et al. |
| 2006/0063993 A1 | 3/2006 | Yu et al. |
| 2006/0064024 A1 | 3/2006 | Schnall |
| 2006/0195028 A1 | 8/2006 | Hannula et al. |
| 2006/0224053 A1 | 10/2006 | Black et al. |
| 2006/0224058 A1 | 10/2006 | Mannheimer |
| 2006/0247501 A1 | 11/2006 | Ali |
| 2006/0253007 A1 | 11/2006 | Cheng et al. |
| 2006/0258921 A1 | 11/2006 | Addison et al. |
| 2007/0073121 A1 | 3/2007 | Hoarau et al. |
| 2007/0073122 A1 | 3/2007 | Hoarau |
| 2007/0073125 A1 | 3/2007 | Hoarau et al. |
| 2007/0073128 A1 | 3/2007 | Hoarau et al. |
| 2007/0078316 A1 | 4/2007 | Hoarau et al. |
| 2007/0078318 A1 | 4/2007 | Kling et al. |
| 2007/0093702 A1* | 4/2007 | Yu et al. ........................ 600/326 |
| 2008/0058622 A1 | 3/2008 | Baker |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076995 A1 | 3/2008 | Hoarau |
| 2008/0076996 A1 | 3/2008 | Hoarau |
| 2008/0077022 A1 | 3/2008 | Baker |
| 2008/0081967 A1 | 4/2008 | Andersohn et al. |
| 2008/0091088 A1 | 4/2008 | Kiani |
| 2008/0200781 A1 | 8/2008 | Van Herpen et al. |
| 2008/0296514 A1 | 12/2008 | Metzger et al. |

FOREIGN PATENT DOCUMENTS

| | | |
|---|---|---|
| EP | 0630203 | 12/1994 |
| EP | 1928303 | 6/2008 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 10216115 | 8/1998 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| WO | WO9101678 | 2/1991 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO2005009221 | 2/2005 |
| WO | WO2007041296 | 4/2007 |
| WO | WO2007051066 | 5/2007 |
| WO | WO 2007122557 A2 * | 11/2007 |
| WO | WO2008039391 | 4/2008 |
| WO | WO2008149342 | 12/2008 |

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Barreto, a.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Barreto, Armando B., et al.; "Adaptive LMS Delay Measurement in dual Blood Volume Pulse Signals for Non-Invasive Monitoring," *IEEE*, pp. 117-120 (1997).

Beard, P.C., et al.; "Miniature optical fibre ultrasonic hydrophone using a Fabry-Perot polymer film interferometer," IEE 1997, Electronics Letters Online No. 19970545, 3 pages.

Beard, P.C., et al.; "Optical fiber photoacoustic-photothermal probe," 1998 Optical Society of America, vol. 23, No. 15, Optics Letters, p. 1235-37.

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Gehring, Harmut, et al.; "The Effects of Motion Artifact and Low Perfusion on the Performance of a New Generation of Pulse

(56) References Cited

OTHER PUBLICATIONS

Oximeters in Volunteers Undergoing Hypoxemia," *Respiratory Care*, Vo. 47, No. 1, pp. 48-60 (Jan. 2002).

Goldman, Julian M.; "Masimo Signal Extraction Pulse Oximetry," *Journal of Clinical Monitoring and Computing*, vol. 16, pp. 475-483 (2000).

Gostt, R., et al.; "Pulse Oximetry Artifact Recognition Algorithm for Computerized Anaesthetic Records," *Journal of Clinical Monitoring and Computing Abstracts*, p. 471 (2002).

Hall, Gregory E., et al.; "Transient Laser Frequency Modulation Spectroscopy," Annu. Rev. Phys. Chem 2000, 51:243-74.

Hamilton, Patrick S., et al.; "Effect of Adaptive Motion-Artifact Reduction on QRS Detection," *Biomedical Instrumentation & Technology*, pp. 197-202 (undated).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Hayes, Matthew J., et al.; "Artifact reduction in photoplethysmography," *Applied Optics*, vol. 37, No. 31, pp. 7437-7446 (Nov. 1998).

Hayes, Matthew J., et al.; "Quantitative evaluation of photoplethysmographic artifact reduction for pulse oximetry," *SPIE*, vol. 3570, pp. 138-147 (Sep. 1998).

Huang, J., et al.; "Low Power Motion Tolerant Pulse Oximetry," *Abstracts*, A7, p. 5103. (undated).

Ince, C.; "The microcirculation is the motor of sepsis," Critical Care 2005, 9(suppl 4):S13-S19 (DOI 10.1186/cc3753), http://ccorum.com/supplements/9/S4/S13.

Johansson, A.; "Neural network for photoplethysmographic respiratory rate monitoring," *Medical & Biological Engineering & Computing*, vol. 41, pp. 242-248 (2003).

Jopling, Michae W., et al.; "Issues in the Laboratory Evaluation of Pulse Oximeter Performance," *Anesth Analg*, vol. 94, pp. S62-S68 (2002).

Kaestle, S.; "An Algorithm for Reliable Processing of Pulse Oximetry Signals Under strong Noise Conditions," *Dissertation Book*, Lubeck University, Germany (1999).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform," pp. II-310-II-311 (undated).

Koch, T., "Monitoring of Organ Dysfunction in Sepsis/Systemic Inflammatory Response Syndrome: Novel Strategies", *J. Am. Soc. Nephrol* 12:S53-S59, 2001.

Lang, P., et al.; "Signal Identification and Quality Indicator™ for Motion Resistant Pulse Oximetry," *Abstracts*, A10, p. S105. (undated).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Masin, Donald I., et al.; "Fetal Transmission Pulse Oximetry," *Proceedings 19th International Conference IEEE/EMBS*, Oct. 30-Nov. 2, 1997; pp. 2326-2329.

Matsuzawa, Y., et al.; "Pulse Oximeter," *Home Care Medicine*, pp. 42-45 (Jul. 2004); (Article in Japanese—contains English summary of article).

Neumann, R., et al.; "Fourier Artifact suppression Technology Provides Reliable $SpO_2$," *Abstracts*, A11, p. S105. (undated).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Odagiri, Y.; "Pulse Wave Measuring Device," *Micromechatronics*, vol. 42, No. 3, pp. 6-11 (undated) (Article in Japanese—contains English summary of article).

Plummer, John L., et al.; "Identification of Movement Artifact by the Nellcor N-200 and N-3000 Pulse Oximeters," *Journal of clinical Monitoring*, vol. 13, pp. 109-113 (1997).

Poets, C. F., et al.; "Detection of movement artifact in recorded pulse oximeter saturation," *Eur. J. Pediatr.*; vol. 156, pp. 808-811 (1997).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp:192-195 (1999).

Spigulis, Janis, et al.; "Optical multi-channel sensing of skin blood pulsations," *Optical Sensing, Proceedings of SPIE*, vol. 5459, pp. 46-53 (2004).

Spronk, P.E., "Bench-to-bedside review: Sepsis is a disease of the microcirculation", Critical Care, (Dec. 2004) vol. 8 No. 6, pp. 462-468.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Vellekoop, I.M., et al., "Demixing Light Paths Inside Disordered Metamaterials," Jan. 7, 2008, vol. 16, No. 1, Optics Express, pp. 67-80.

Vellekoop, I.M., et al.; "Focusing Coherent Light Through Opaque Strongly Scattering Media," Aug. 15, 2007 Optical Society of America, vol. 32, No. 16, Optics Letters, pp. 2309-2311.

Vincente, L.M., et al.; "Adaptive Pre-Processing of Photoplethysmographic Blood Volume Pulse Measurements," pp. 114-117 (1996).

Ware, L.B., "Measuring microvascular blood flow in sepsis—a continuing challenge", The Lancet, vol. 360 (Oct. 19, 2002) www.thelancet.com pp. 1187-1188.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

\* cited by examiner

PHOTOACOUSTIC SPECTROSCOPY METHOD AND SYSTEM TO DISCERN SEPSIS FROM SHOCK

RELATED APPLICATIONS

This application claims the benefit of U.S. Provisional Application No. 61/245580, filed Sep. 24, 2009, which application is hereby incorporated by reference.

BACKGROUND

The present disclosure relates generally to medical devices and, more particularly, to the use of continuous wave photoacoustic spectroscopy and other medical monitoring data to help distinguish sepsis from shock.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

For example, clinicians may wish to monitor a patient's blood flow and blood oxygen saturation to assess cardiac function. Deviation from normal or expected values may alert a clinician to the presence of a particular clinical condition. A patient's microcirculatory system, which includes the arterioles and capillaries, is involved in delivering blood to various organs. A change in blood delivery to these organs may be an indication of injury or disease. By monitoring changes in microcirculation, a clinician may be able to diagnose or monitor diseases in particular organs or tissues. In addition, changes in microcirculation may predict systemic changes that present earlier or more profound microcirculatory changes, followed by changes in blood flow to larger vessels. For example, in cases of shock or pathogenic infection, a clinical response may include shunting of blood from the microcirculatory system to the larger vessels in an attempt to increase blood flow and prevent injury to primary organs (e.g., the brain and heart) while temporarily decreasing blood flow to secondary organs (e.g., the gastrointestinal system or the skin).

Changes in microcirculation may be monitored by techniques for assessing blood volume. Some techniques may be invasive and involve the use of radioisotopes or other tagged blood indicators. The indicators may be tracked through the circulation to estimate the blood volume. Many of these techniques involve indirect assessment of blood volume by measuring the density or concentration of certain blood constituents. For example, sound velocity measurements may be used for measuring several hemodynamic parameters. However, such sensors utilize a linear approximation of a non-linear relationship between the sound velocity and the density of the blood. This approximation may limit the accuracy of the technique. In addition, these techniques may not be suitable for assessing local changes in microcirculation.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
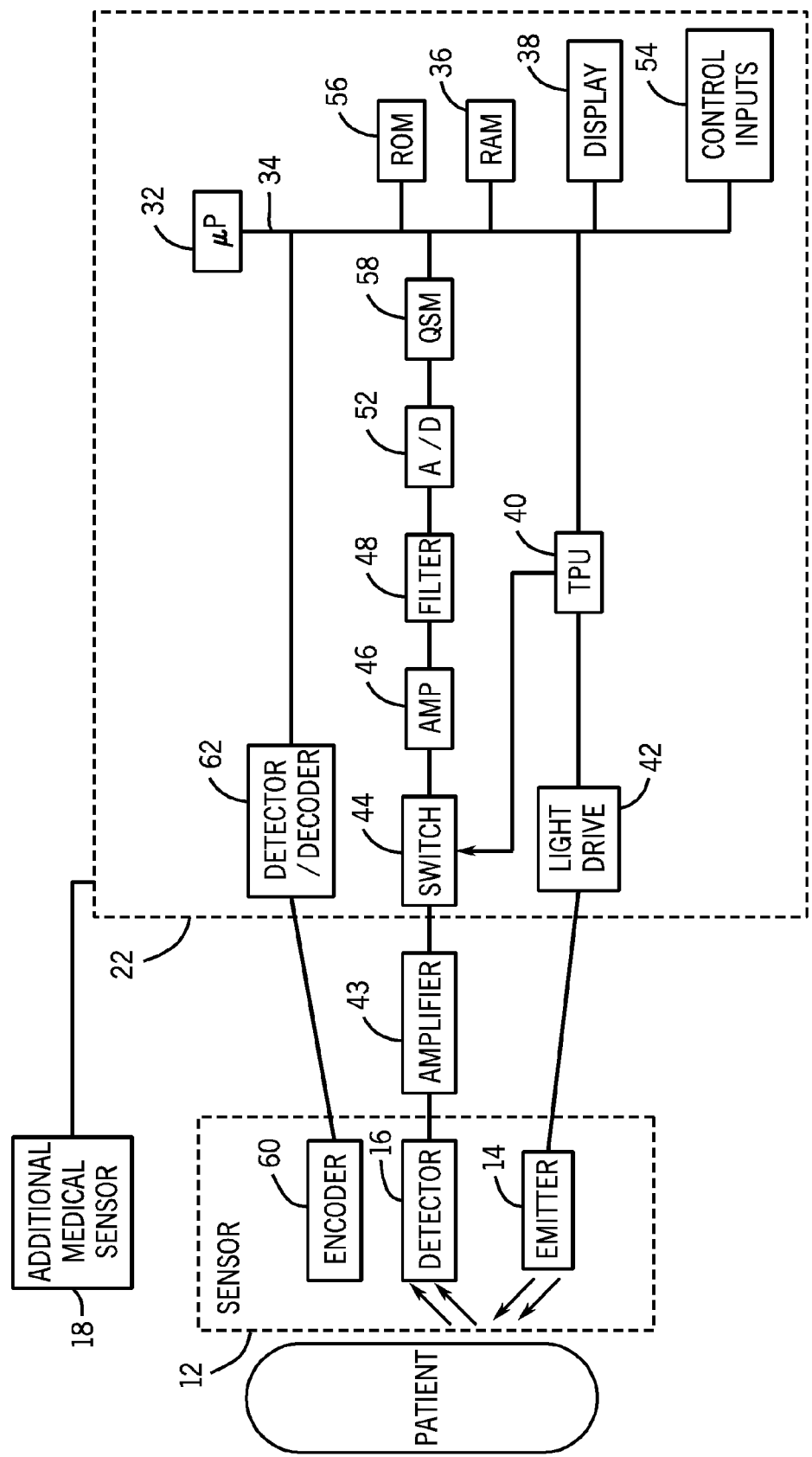
FIG. 1 is a block diagram of a patient monitor in accordance with an embodiment.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Monitoring a patient's microcirculation may be complex, particularly when using techniques that involve estimation of total blood volume. As provided herein, photoacoustic spectroscopy may be used to noninvasively monitor microcirculation in a patient. Such monitoring may provide information about the patient's clinical condition and, in embodiments, may allow clinicians to diagnose patients based at least in part on changes in microcirculation, Sensors as provided may be applied to a patient's skin or mucosal tissue to monitor the microcirculatory parameters. For example, such sensors may be suitable for use on any area of a patient with a sufficient density of microcirculatory vessels. Such areas include digits, ears, cheeks, the lingual and sublingual area, and/or the upper respiratory tract (e.g., the esophagus, trachea or lungs, which may be accessible through tracheostomy tubes or endotracheal tubes). Further, such sensors may be used to monitor organ tissue that may be accessible while a patient is undergoing surgical treatment. In one embodiment, patients undergoing cardiac surgery may be monitored for microcirculatory changes to assess cardiac function and possible onset of shock or sepsis during the operation.

Accurate determination of changes in a patient's microcirculation may allow clinicians to begin appropriate therapy to avert complications. In particular, tracking microcirculation may help distinguish between critical conditions such as shock and sepsis, which have similar presentation patterns but which may involve significantly different treatment plans. Shock is characterized by a temporary decrease in microcirculation as the patient's systemic shock response is activated and a subsequent microcirculation increase or rebound as the shock response progresses. In sepsis, a microcirculation decrease typically does not rebound. By accurately monitoring microcirculation, for example with photoacoustic spectroscopy, a clinician may establish an earlier diagnosis of shock or sepsis, which may provide clinical benefits to the patient.

Photoacoustic spectroscopy involves a light source that, when emitted into a tissue, is absorbed by certain components of the tissue and/or blood, The absorption and non-radiative relaxation process leads to local warming and pressure fluctuations, which may be detected in the form of acoustic radiation (e.g., ultrasound). The detected acoustic radiation may be correlated to a density or concentration of a particular absorber that absorbs at the wavelength of the emitted light. By emitting a wavelength absorbed by components of the blood, photoacoustic spectroscopy may be used to estimate microcirculatory blood volume at particular measurement sites and to track changes in the microcirculatory system. Photoacoustic spectroscopy may provide certain advantages for the examination of microcirculation. Because the technique is spectroscopic, the measurements may be performed noninvasively. In addition, photoacoustic spectroscopy may be suitable for tracking the clinical progress of patients who are at risk for developing conditions such as sepsis or shock.

Provided herein are systems, sensors, and methods for monitoring microcirculation. When such systems are used in conjunction with a photoacoustic spectroscopy sensor, a medical monitor may assess one or more parameters indicative of microcirculation, including blood volume or flow in a tissue bed perfused with microcirculatory vessels, the depth or distribution of microcirculatory vessels, or the concentration of blood constituents in the microcirculatory vessels. Such systems may also be used to compare the parameters of the smallest microcirculatory vessels to relatively larger microcirculatory vessels. Because changes in microcirculation may be seen first in the smallest vessels, the sensitivity of a photoacoustic spectroscopy sensor that allows assessment of even very small vessels may allow earlier monitoring of microcirculatory changes that may be associated with shock or sepsis.

FIG. 1 shows a system 10 that may be used for monitoring microcirculation. The system 10 includes a photoacoustic spectroscopy sensor 12 with a light source 14 and acoustic detector 16. It is envisioned that both pulsed and continuous wave light sources may be used for the sensor 12. While certain photoacoustic monitoring techniques may employ light sources that emit pulsed radiation, in continuous wave photoacoustic spectroscopy, the light source is not pulsed. This allows for longer-term monitoring of tissue. Because pulsed wave sources typically use higher power, they may eventually undesirably increase the temperature of the tissue, which may interfere with the measurements. Continuous wave light sources are typically lower power, and, thus, may result in less heating of the tissue. Because microcirculation takes place in relatively small blood vessels, such undesirable temperature changes may have a significant effect on the blood flow in those vessels and may interfere with sensor measurements, which may depend on much smaller effects that may be swamped by increased blood flow or large temperature changes.

The sensor assembly 10 includes a light emitter 14 and an acoustic detector 16 that may be of any suitable type. As noted, the emitter 14 may be pulsed or continuous wave. For example, the emitter 14 may be one or more light emitting diodes adapted to transmit one or more wavelengths of light in the red to infrared range, and the detector 16 may one or more ultrasound receivers configured to receive ultrasound waves generated by the tissue in response to the emitted light. In specific embodiments, the emitter 14 may be a laser diode or a vertical cavity surface emitting laser (VCSEL). The laser diode may be a tunable laser, such that a single diode may be tuned to various wavelengths corresponding to a number of absorbers. Depending on the particular arrangement of the photoacoustic sensor 12, the emitter 14 may be associated with an optical fiber for transmitting the emitted light into the tissue. The light may be any suitable wavelength corresponding to the wavelengths absorbed by certain constituents in the blood. For example, wavelengths between about 500 nm to about 600 nm, corresponding with green visible light, may be absorbed by deoxyhemoglobin and oxyhemoglobin. In other embodiments, red and near infrared wavelengths may be used. Further, the emitted light may be modulated at any suitable frequency, such as 10 mHz or 100 mHz. In certain embodiments, different frequency modulation may be used to distinguish photon density waves. Based on the propagation of the photon density waves, the acoustic effect may vary in a corresponding manner.

If the emitter 14 emits a continuous wave, the corresponding acoustic detector 16 may be a standard receiver, as compared with pulsed light, which may generate an acoustic effect that involves a more complex receiver to capture the resultant acoustic wave. Further, the acoustic wave generated by the continuous wave may have a higher signal to noise ratio relative to a pulse wave. In certain embodiments, the detector 16 may be a low finesse Fabry-Perot interferometer mounted at the tip of an optical fiber. In such an embodiment, the incident acoustic wave emanating from the probed tissue modulates the thickness of the thin polymer film. This produces a corresponding intensity modulation of the light reflected from the film. Accordingly, the acoustic wave is converted to optical information, which is transmitted through the optical fiber to an upstream optical detector, which may be any suitable detector. The change in phase of the detected light may be detected via an appropriate interferometry device. The use of the thin film allows high sensitivity to be achieved, even for films of micrometer or tens of micrometers in thickness. The thin film may be a 0.25 mm diameter disk of 50 micrometer thickness polyethylene terepthalate with an at least partially optically reflective (e.g., 40% reflective) aluminum coating on one side and a mirror reflective coating on the other (e.g., 100% reflective) that form the mirrors of the interferometer. The optical fiber may be any suitable fiber, such as a 50 micrometer core silica multimode fiber of numerical aperture 0.1 and an outer diameter of 0.25 mm.

The system 10 may, in embodiments, also include any number or combination of additional medical sensors 18 or sensing components for providing information related to patient parameters that may be used in conjunction with the photoacoustic spectroscopy sensor 12. For example, suitable sensors may include sensors for determining blood pressure, blood constituents (e.g., oxygen saturation), respiration rate, respiration effort, heart rate, patient temperature, or cardiac output. Such information may be used in conjunction with microcirculation information to determine if a patient is shock or has a systemic septic infection. By way of example, FIG. 1 shows a pulse oximetry sensor 18 that may be associated with the system 10. However, it should be understood that pulse oximetry sensor 18 is merely illustrative of a medical sensor that may be used in conjunction with the monitoring system 10. In certain embodiments, photoacoustic spectroscopy sensor 12 may be a multi-parameter sensor, for example with a unitary housing, that includes additional optical components for pulse oximetry sensing or other cardiac or blood constituent sensing.

The monitor 22 may receive signals, for example from the photoacoustic spectroscopy sensor 12 and, in embodiments, from one or more additional sensors 18, to determine if a patient is undergoing microcirculation changes that are indicative of shock or sepsis. In embodiments in which sensor 18 is a pulse oximetry sensor, the pulse oximetry signal may generate a plethysmographic waveform, which may be further processed by the monitor 22. The monitor 22 may receive and further process a signal from the photoacoustic spectroscopy sensor 12 to determine an indication related to microcirculatory parameters and, in embodiments, one or more indications representative of a patient's likelihood of being septic or in shock.

The monitor 22 may include a microprocessor 32 coupled to an internal bus 34. Also connected to the bus may be a RAM memory 36 and a display 38. A time processing unit (TPU) 40 may provide timing control signals to light drive circuitry 42, which controls when an optical sensor (e.g., pulse oximetry sensor 20, carbon dioxide sensor 24, or tissue water fraction sensor 26) is activated, and, if multiple light sources are used, the multiplexed timing for the different light sources. TPU 40 may also control the gating-in of signals from the sensor 12 and a switching circuit 44. In certain embodiments, if the signal to noise ratio of the sensor is high enough, the amplifier 43 may be omitted. These signals are sampled at the proper time, depending at least in part upon which of multiple light sources is activated, if multiple light sources are used. The received signal from the sensor 12 may be passed through an amplifier 46, a low pass filter 48, and an analog-to-digital converter 50. The digital data may then be stored in a queued serial module (QSM) 52, for later downloading to RAM 46 or ROM 56 as QSM 52 fills up.

In an embodiment, based at least in part upon the received signals corresponding to the acoustic waves received by detector 16 (e.g., an ultrasound receiver) of the sensor 12, microprocessor 32 may calculate the microcirculation parameters using various algorithms. In addition, the microprocessor 32 may calculate other medical parameters based on information from one or more additional medical sensors 18. A patient diagnosis of sepsis or shock may be made based on input signals from the sensor 12 and, in embodiments, other sensors 18 (e.g., pulse oximetry sensor), or caregiver inputs to control inputs 54. For example, the caregiver may input a patient's age, weight, gender, or information about the patient's clinical condition that may be relevant to the accurate diagnosis of sepsis or shock. These algorithms may employ certain coefficients, which may be empirically determined, and may correspond to the wavelength of light used. In addition, the algorithms may employ additional correction coefficients. The algorithms and coefficients may be stored in a ROM 56 or other suitable computer-readable storage medium and accessed and operated according to microprocessor 32 instructions. In one embodiment, the correction coefficients may be provided as a lookup table. In addition, the sensor 12 may include certain data storage elements, such as an encoder 60, that may encode information related to the characteristics of the sensor 12, including information about the emitter 14 and the detector 16. The information may be accessed by detector/decoder 62, located on the monitor 22.

Parameters related to a patient's microcirculation may be determined based on the signal received from the photoacoustic spectroscopy sensor 12, As provided, monitoring microcirculatory changes may help distinguish between sepsis and shock for patients who have one condition, but not the other. The stages of sepsis present similarly to the stages of shock, with the exception of certain differences in the microcirculatory parameters. If the distinction is made between sepsis and shock at a suitable stage in the progression, appropriate therapy may be started. In particular, shock or physiological shock may result from any serious assault on the body's homeostatic mechanisms, whether from hemorrhage, trauma, burn injury, myocardial infarction or sepsis. Shock consists of widespread hypoperfusion at the tissue level, due to reduction of blood volume, reduction of cardiac output or redistribution of effective circulation, This results in insufficient delivery of oxygen and metabolites to the cells and inadequate clearance of metabolic byproducts. The resultant shift from aerobic to anaerobic cellular metabolism leads to the accumulation of lactic acid in the tissues. Specific types of shock may include cardiogeneic shock, hypovolemic shock, anaphylactic shock, neurogenic shock, and septic shock.

While sepsis also involves a systemic host involvement, sepsis generally refers to a host defense response that accompanies a microbial invasion. Sepsis may include conditions such as terms as septicemia, septic syndrome and septic response. The term sepsis may be associated with any systemic response to overwhelming infection or other severe insult, including: 1) disseminated microorganisms or their biochemical products from a site of infection, 2) microorganisms or their biochemical products without an infected primary source and 3) local inflammatory mediators from an infectious source or from a sterile site without the participation of microorganisms or their biochemical products. Organisms commonly involved in provoking sepsis include Gram positive bacteria, Gram negative bacteria and fungi. Sepsis responses may also follow non-infectious events such as acute pancreatitis. Similar biological events are understood to be able to lead to the septic response following an infectious or a non-infectious insult. The physiological and biochemical responses characterizing sepsis include: 1) hyperdynamic cardiac parameters, 2) a reduced peripheral vascular resistance, 3) a narrowed arteriovenous oxygen difference and 4) elevated serum lactate levels.

Figure 2:
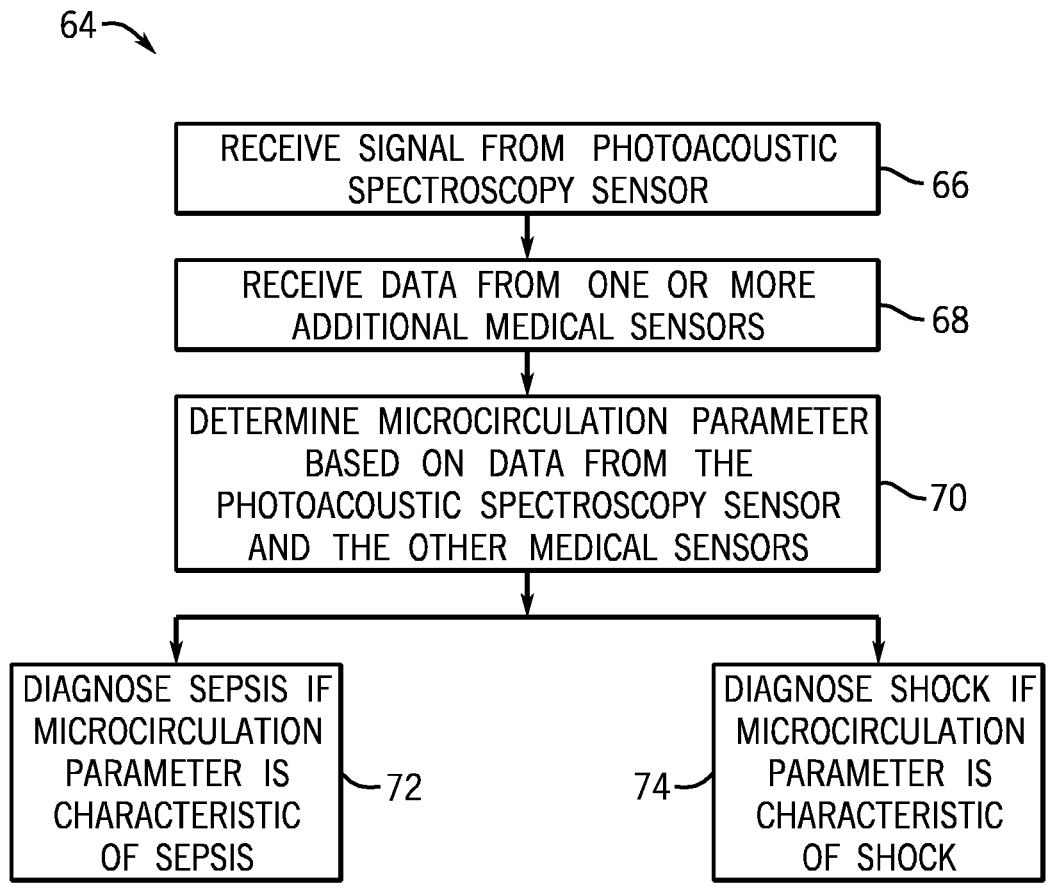
FIG. 2 is a block diagram of a method of distinguishing sepsis from shock in accordance with an embodiment.

FIG. 2 is a process flow diagram illustrating a method 64 for distinguishing between sepsis and shock in accordance with some embodiments. The method may be performed as an automated procedure by a system, such as system 10. In addition, certain steps of the method may be performed by a processor, or a processor-based device such as a patient monitor 22 that includes instructions for implementing certain steps of the method 64.

According to an embodiment, the method 64 begins with obtaining a signal from detector 16 associated with the photoacoustic spectroscopy sensor 12 at step 66. While microcirculation data may be determined from signal from the photoacoustic spectroscopy sensor 12 alone, in certain embodiments, data relating to one or more additional patient parameters may obtained at step 68 to augment the data from the continuous wave photoacoustic spectroscopy sensor 12. The data relating to one or more patient parameters may be calculated from signals received from additional patient sensors 18, e.g., a pulse oximetry sensor, a blood pressure sensor, a respiration rate or effort sensor, and/or cardiac function sensors. In addition, the data relating to one or more patient parameters may be manually input by a healthcare provider.

The monitor 22 may perform analysis of the signal from the photoacoustic spectroscopy sensor 12 and calculation of the microcirculation parameters at step 70 based on the photoacoustic spectroscopy signal obtained at step 66 and any additional patient parameter data obtained at step 68. Such parameters may include blood flow or volume, whereby a decrease in blood flow may be indicated by a corresponding decrease in intensity of the signal from the acoustic detector 16 or a corresponding increase in the time of flight of the acoustic wave transmission.

For example, in one embodiment, the microcirculation parameter, such as blood volume or flow, is examined over a predetermined time window to assess changes. If the change in the microcirculation parameter is indicative of sepsis, a preliminary diagnosis of sepsis may be made and an appropriate treatment protocol may be ordered at step 72. If the change in the microcirculation parameter is indicative of shock, a preliminary diagnosis of shock may be made and an appropriate treatment protocol may be ordered at step 74. For example, because sepsis is associated with infection, a sepsis treatment protocol may involve aggressive antibiotic treatment and monitoring of infection, while a shock protocol may involve stabilizing the patient and non-antibiotic pharmaceutical intervention. Further, patients with sepsis and shock may benefit from hydration or volume provision therapy, although such treatment may be less effective in patients with sepsis that are experiencing severe volume redistribution away from the microcirculation. In such patients, vasodilation (e.g., mediated by agents such as nitroglycerin) may be effective in promoting microcirculation increases.

Both sepsis and shock present with decreased microcirculation. However, in shock, the microcirculation rebounds within a relatively short time frame (e.g., several minutes or within 1-2 hours). In sepsis, the microcirculation decrease is maintained over the duration of the condition. Septic shock, a subset of shock caused by sepsis, may be associated with depressed microcirculation that is maintained throughout, i.e., although the patient is in shock, the overlapping condition of sepsis may overwhelm the diagnosis, meaning that the effect on the microcirculation parameters is more similar to sepsis than shock. Accordingly, distinguishing between sepsis and shock may involve monitoring one or more microcirculation parameters over a time window and detecting a presence or absence of a characteristic rebound in microcirculation. If there is a rebound, a diagnosis of shock may be set forth. If there is no rebound, a diagnosis of sepsis may be more likely. Appropriate time windows to assess any microcirculation rebound may include ten minute monitoring windows or windows of up to an hour or two hours.

In addition, such monitoring may include any appropriate visual indication displayed on the monitor 22 or any appropriate audio indication. For example, any decrease in a microcirculation parameter below a predetermined threshold or outside of a predetermined range may trigger an alarm. Such an alarm may include an indication that either shock or sepsis may be a possible clinical complication for the monitored patient. Further, additional indications may include text or other alerts to inform a caregiver if shock or sepsis is suspected. In one embodiment, a graphical representation of the microcirculation parameter may be displayed. A graph of a microcirculation parameter over time may provide a visual representation of a rebound (e.g., shock) or a generally depressed state (e.g., sepsis) that may provide information to clinicians.

Figure 3:
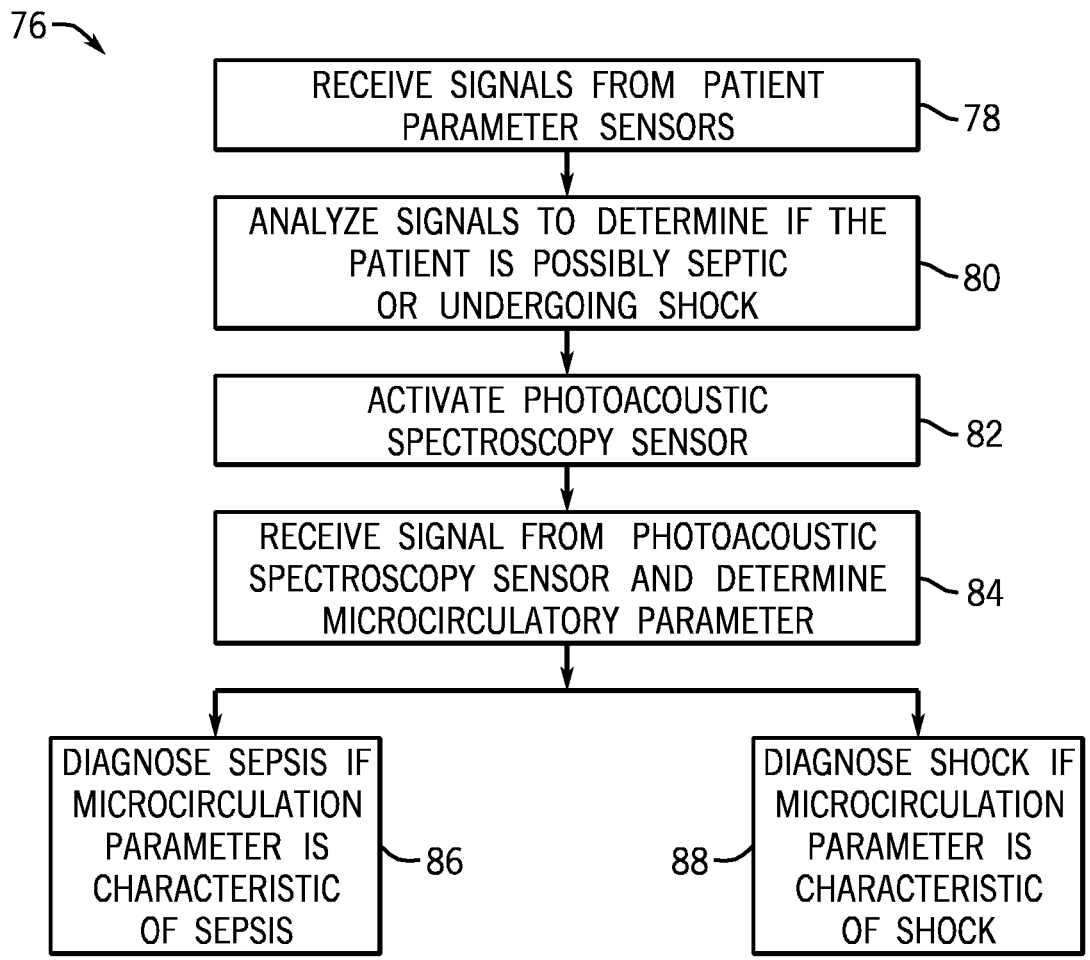
FIG. 3 is a block diagram of a method of monitoring for early signs of sepsis or shock.

Monitoring for shock or sepsis may involve additional monitoring of patient parameters. In the flow diagram 76 of FIG. 3, a patient undergoing normal monitoring may also be monitored with a photoacoustic sensor 12 that is activated or applied when other clinical indications point to shock or sepsis. A patient may monitored for parameters including one or more of temperature, heart rate, respiration rate, respiration effort, or blood pressure at step 78. Such monitoring may be part of standard orders for patients in the emergency room or in a critical care unit. The signals from these sensors may be analyzed for patterns indicative of shock or sepsis at step 80. For example, a decrease in temperature, an increase in blood pressure, an increase in heart rate, an increase in respiratory rate, or an increase in respiration effort may all be indicative of a serious clinical condition such as shock or sepsis. When one or all of these associated symptoms are detected, a monitor may provide an alert to a caregiver to apply a photoacoustic sensor 12. Alternatively, the photoacoustic sensor 12 may be part of a sensor assembly that includes other sensor types that provide the monitoring data in step 78 and that is already in place on the patient. If it is determined that shock or sepsis is possible, a light drive 42 may activate the emitter 14 to emit light into the tissue at step 82. When the data from the photoacoustic sensor 12 is received at step 84, the data may be analyzed to determine if the microcirculation parameter is indicative of sepsis at step 86 or if the parameter is indicative of shock at step 88. Depending on the determination, a diagnosis of shock or sepsis may be made and the appropriate intervention begun.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of monitoring a patient, comprising: using a processor to perform the steps of: controlling a driver of a light source of a photoacoustic spectroscopy sensor, wherein the light source is configured to emit one or more wavelengths of light; receiving a signal from the photoacoustic spectroscopy sensor, wherein the signal is representative of a microcirculatory parameter of a patient; calculating the microcirculatory parameter based at least in part on the signal via one or more algorithms stored in a memory; determining whether the patient has shock or sepsis based at least in part on the microcirculatory parameter, wherein determining if the patient has sepsis comprises monitoring the microcirculatory parameter over a period of time and determining if a decrease in the microcirculatory parameter is not followed by a rise in the microcirculatory parameter; and providing an indication of the microcirculatory parameter on a display.

2. The method of claim 1, comprising triggering an alarm when the micro circulatory parameter is less than a predetermined level or outside of a predetermined range.

3. The method of claim 1, comprising;
controlling a driver of a light emitter of a second sensor to receive a second signal related to a clinical parameter, wherein the clinical parameter is of one or more of the patient's blood pressure, a heart rate, a respiration rate, a respiration effort, or a temperature;
determining if one or more of the patient's blood pressure, the heart rate, the respiration rate, the respiration effort, or the temperature is indicative of possible shock or sepsis; and
activating the driver of light source of the photoacoustic spectroscopy sensor if the clinical parameter is indicative of possible shock or sepsis.

4. The method of claim 1, comprising providing an indication on the display that shock therapy should be started if the patient has shock.

5. The method of claim 1, comprising providing an indication on the display that sepsis therapy should be started if the patient has sepsis.

6. The method of claim 1, wherein determining if the patient has shock comprises monitoring the microcirculatory parameter over a period of time and determining if a decrease in the microcirculatory parameter is followed by a rise in the microcirculatory parameter.

7. A method of monitoring a patient, comprising: using a processor: receiving a first signal from a first sensor related to a clinical parameter, wherein the clinical parameter is one or more of a patient's blood pressure, a heart rate, a cardiac output, blood constituents, a respiration rate, a respiration effort, or a temperature; determining if the first signal is associated with a possible sepsis or a possible shock condition; activating a photoacoustic sensor if the first signal is associated with the possible sepsis or the possible shock condition, wherein activating the photoacoustic sensor comprises providing instructions to drive a light emitter of the photoacoustic sensor; receiving a second signal from the photoacoustic sensor related to one or more microcirculatory parameters of the patient; calculating a microcirculatory parameter of the patient based on the second signal; and distinguishing between sepsis or shock based at least in part on the determined microcirculatory parameter, wherein the distinguishing comprises: determining that the patient has shock based on a decrease in the microcirculatory parameter followed by a rise in the microcirculatory parameter; and determining that the patient has sepsis based on a decrease in the microcirculatory parameter not followed by a rise in the microcirculatory parameter.

8. The method of claim 7, comprising triggering an alarm when the microcirculatory parameter is less than a predetermined level or outside of a predetermined range.

9. The method of claim 7, wherein the microcirculatory parameter is related to one or more of the patient's blood flow, the patient's blood volume, a depth or distribution of the patient's microcirculatory vessels, or a concentration of blood constituents in the patient's microcirculatory vessels.

10. A method of monitoring a patient, comprising:
using a processor to perform the steps of:
controlling a driver of a light emitter of a first sensor;
receiving a first signal from the first sensor related to a clinical parameter, wherein the clinical parameter is associated with a possible sepsis or a possible shock condition:
activating a driver of a light source of a photoacoustic spectroscopy sensor based on an increase or decrease in the clinical parameter, wherein the light source is configured to emit one or more wavelengths of light;
receiving a second signal from an acoustic detector of the photoacoustic spectroscopy sensor, wherein the second signal is representative of a blood flow parameter of a patient;
determining the blood flow parameter based at least in part on the second signal;
determining whether the patient has shock or sepsis based at least in part on the blood flow parameter, wherein determining if the patient has shock comprises monitoring the blood flow parameter over a period of time and determining if a decrease in the blood flow parameter is followed by a rise in the blood flow parameter; and
providing an indication of the blood flow parameter over the period of time on a display, comprising providing a indication of shock if the patient has shock and an indication of sepsis if the patient has sepsis.

11. The method of claim 7, wherein the first signal is associated with the possible sepsis or the possible shock condition if one or more of an decrease in the temperature, an increase in the blood pressure, an increase in the heart rate, an increase in the respiratory rate, or an increase in the respiration effort is determined.

12. The method of claim 7, wherein the first sensor is a pulse oximetry sensor.

13. The method of claim 7, wherein the first sensor is a blood pressure sensor.

14. The method of claim 7, wherein the first sensor is a respiration rate sensor or a respiration effort sensor.

15. The method of claim 7, wherein the first sensor is a cardiac function sensor.

16. The method of claim 7, wherein the first sensor is a temperature sensor.

* * * * *